United States Patent
Savage-Erickson

(10) Patent No.: US 8,609,127 B2
(45) Date of Patent: Dec. 17, 2013

(54) MEDICAL IMPLANT WITH BIOACTIVE MATERIAL AND METHOD OF MAKING THE MEDICAL IMPLANT

(75) Inventor: Heather M. Savage-Erickson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 604 days.

(21) Appl. No.: 12/418,321

(22) Filed: Apr. 3, 2009

(65) Prior Publication Data

US 2010/0255053 A1 Oct. 7, 2010

(51) Int. Cl.
- *A61F 2/28* (2006.01)
- *A61L 27/16* (2006.01)
- *A61L 27/56* (2006.01)
- *A61L 27/54* (2006.01)
- *A61L 27/12* (2006.01)

(52) U.S. Cl.
USPC ..... 424/426; 424/423; 623/23.63; 623/23.75; 623/16.11

(58) Field of Classification Search
None
See application file for complete search history.

(56) References Cited

U.S. PATENT DOCUMENTS

| | | | |
|---|---|---|---|
| 3,616,841 A | 11/1971 | Walz | |
| 3,790,365 A | 2/1974 | Niebylski | |
| 3,816,952 A | 6/1974 | Niebyski | |
| 4,728,570 A | 3/1988 | Ashman | |
| 4,969,906 A | 11/1990 | Kronmann | |
| 5,281,251 A | 1/1994 | Kenny | |
| 5,282,861 A | 2/1994 | Kaplan | |
| 5,306,673 A | 4/1994 | Hermansson | |
| 6,136,029 A | 10/2000 | Johnson | |
| 6,383,519 B1 | 5/2002 | Sapieszko | |
| 6,572,619 B2 | 6/2003 | Santilli | |
| 6,673,075 B2 | 1/2004 | Santilli | |
| 6,863,899 B2 | 3/2005 | Koblish | |
| 6,887,488 B2 | 5/2005 | Cui | |
| 6,974,625 B2 | 12/2005 | Hunter | |
| 6,977,095 B1 | 12/2005 | Marx | |
| 7,230,039 B2 | 6/2007 | Trieu | |
| 7,250,550 B2 | 7/2007 | Overby | |
| 2002/0143403 A1 * | 10/2002 | Vaidyanathan et al. ... | 623/23.51 |
| 2002/0169066 A1 | 11/2002 | Cassidy | |
| 2003/0220696 A1 | 11/2003 | Levine | |
| 2004/0024081 A1 | 2/2004 | Trieu | |
| 2004/0243241 A1 * | 12/2004 | Istephanous et al. ...... | 623/17.14 |
| 2005/0112397 A1 | 5/2005 | Rolfe | |
| 2005/0201987 A1 | 9/2005 | Pirhonen | |
| 2005/0246021 A1 | 11/2005 | Ringesien | |
| 2006/0088601 A1 | 4/2006 | Overby | |
| 2006/0110306 A1 | 5/2006 | Chow | |
| 2006/0147332 A1 | 7/2006 | Jones | |
| 2006/0271201 A1 * | 11/2006 | Kumar et al. ................. | 623/23.5 |
| 2006/0276900 A1 | 12/2006 | Carpenter | |
| 2007/0093912 A1 | 4/2007 | Borden | |
| 2007/0122447 A1 | 5/2007 | Koblish | |
| 2007/0187857 A1 | 8/2007 | Riley | |
| 2007/0250045 A1 * | 10/2007 | Trieu ......................... | 604/890.1 |
| 2007/0254007 A1 | 11/2007 | Bumgardner | |
| 2008/0014242 A1 | 1/2008 | Overby | |
| 2008/0206297 A1 * | 8/2008 | Roeder et al. ................. | 424/422 |

OTHER PUBLICATIONS

Kaito,T et al: "Potentiation of the activity of bone morphogenetic protein-2 in bone regeneration by a PLA-PEG/hydroxyapatite composite" Boimaterials, Elsevier Science Publishers BV., Barking,GB LNKD_DOI:10.1016/J. Biomaterials. 2004.02.010, vol. 26, No. 1. Jan. 1, 2005, pp. 73-79, XPO 25280936 ISSN: 0142-9612 [retreived on Jan. 1, 2005] p. 74, paragraph 5-paragraph 8.

* cited by examiner

*Primary Examiner* — Robert A Wax
*Assistant Examiner* — H. Sarah Park
(74) *Attorney, Agent, or Firm* — Sorell Lenna & Schmidt LLP

(57) ABSTRACT

Embodiments of the invention include a medical device and a method of manufacturing a medical device having a porous scaffold in combination with a bioactive material. In some embodiments, particularly limited thicknesses of the bioactive material are applied within pores of the porous structure.

18 Claims, 1 Drawing Sheet

MEDICAL IMPLANT WITH BIOACTIVE MATERIAL AND METHOD OF MAKING THE MEDICAL IMPLANT

FIELD OF THE INVENTION

The present invention relates generally to the field of medical implants and methods of making medical implants, and more particularly relates to a medical implant with a porous scaffold and a bioactive material disposed within the porous scaffold and related methods of making the medical implant.

BACKGROUND

It is advantageous in many orthopedic applications for bone to grow into, around and/or even completely through, implants designed to support or replace various musculoskeletal structures. Many porous structures exist in the prior art that are designed to receive growing bone or other musculoskeletal tissue. In combination with and in addition to these structures, various bioactive materials are known that passively support or promote the growth of bone and other tissues. Substances that passively support the growth of bone are known as osteoconductive. Osteoconductive substances passively support the ingrowth of bone by being conducive to the growth of vascular structures and osteoprogenitor cells necessary for the growth of bone. Substances that actively stimulate or promote the growth of bone are known as osteogenic or osteoinductive. Specifically, osteogenic substances stimulate the formation of bone, and osteoinductive materials support the mitogenesis of undifferentiated perivascular mesenchymal cells. This osteoinductive activity may lead to the formation of osteoprogenitor cells with the capacity to form new bone.

It is a continuing challenge in the art to produce implants that provide adequate structural support while also providing structures into which bone will actively grow. Some implants include structures that are appropriately shaped to receive growing bone and support musculoskeletal tissues, but lack effective placement of osteoconductive or osteoinductive materials to support the growth of bone throughout or where most advantageous. Other implants include sufficient osteoconductive or osteoinductive materials, but are not formed to provide adequate structural stability and/or to permit bone to grow into portions of the implant that would be advantageous. Therefore, a need exists for implants and for methods of making implants that are both structurally adequate and support or promote bone growth into or through the implants.

SUMMARY

One embodiment of the invention is a method of manufacturing a medical implant with a first side and an opposite second side. The method includes providing a porous scaffold with one or more tunnels that pass more than half way through the medical implant between the first side and the second side, and depositing a bioactive material in a thickness of less than about ten microns on an interior wall of one or more of the tunnels at least half way through the medical implant between the first side and the second side.

Another embodiment of the invention is a method of manufacturing a medical implant with a first side and an opposite second side. The method includes providing a porous scaffold with one or more tunnels that pass more than half way through the medical implant between the first side and the second side. The method further includes depositing a bioactive material by spraying the bioactive material on an interior wall of one or more of the tunnels at least half way through the medical implant between the first side and the second side.

An embodiment of the invention is a medical implant having a first side and an opposite second side. The medical implant may include a porous scaffold with multiple pores defining open volumes that connect at least between the first side and the second side. The porous scaffold may also include a scaffold structure that makes up between about thirty percent and about eighty percent by volume of the porous scaffold, and the multiple pores include walls defining interfaces between the scaffold structure and the pores. The medical implant also includes a bioactive material on average less than about ten microns thick that is coupled to substantially all of the walls of the porous scaffold. Multiple paths through the pores between the first side and the second side of some embodiments remain at least in part open for passage of a fluid through the porous scaffold and the bioactive material.

Yet another embodiment of the invention is a medical implant with a first side and an opposite second side. The medical implant includes a support means with one or more tunnels that pass more than half way through the medical implant between the first side and the second side and a bioactive means deposited on an interior wall of one or more of the tunnels at least half way through the medical implant between the first side and the second side.

DETAILED DESCRIPTION

Figure 1:
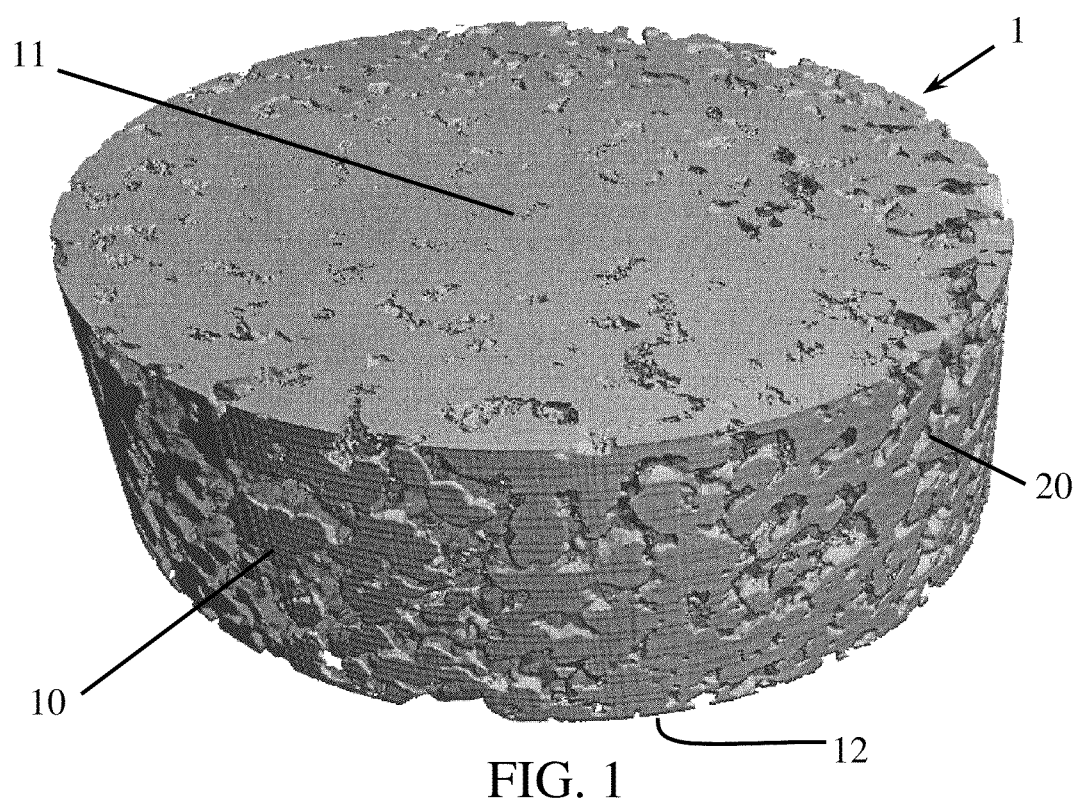
FIG. 1 is a perspective view of an embodiment of a medical implant.
Figure 2:
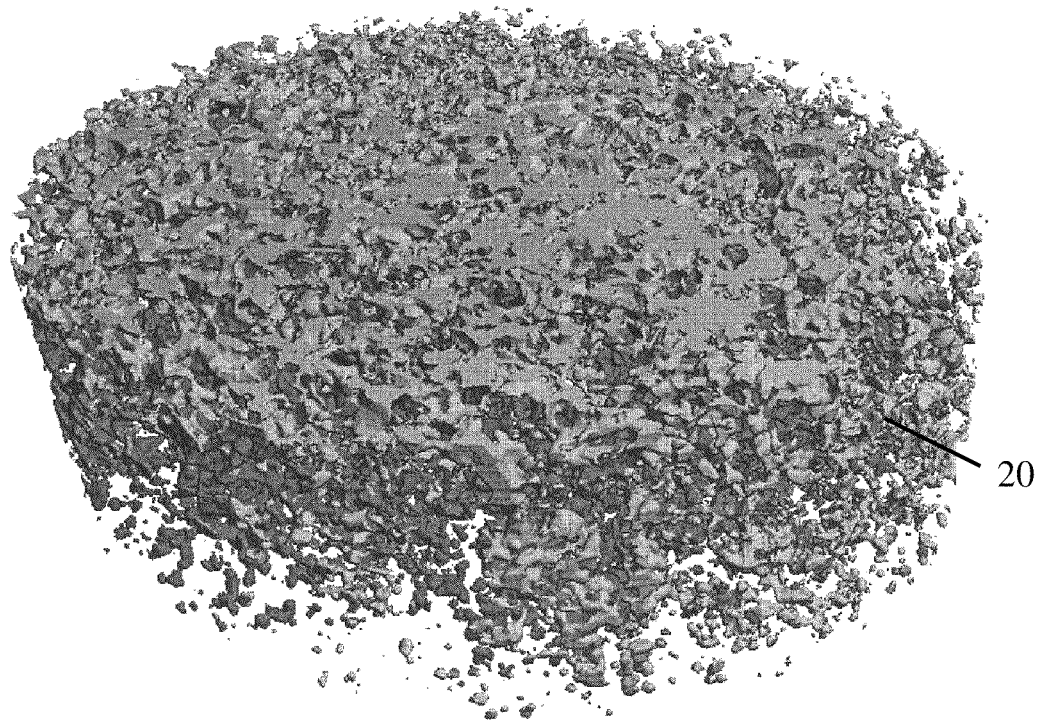
FIG. 2 is a perspective view of the embodiment of the medical implant of FIG. 1 with a porous scaffold portion of the medical implant removed to illustrate other components.

An embodiment of a medical implant 1 is illustrated in FIGS. 1 and 2. A porous scaffold 10 is shown in combination with a bioactive material 20. In FIG. 2, the porous scaffold 10 has been removed from the illustration to show the configuration of the bioactive material 20 within the porous scaffold 10. The medical implant 1 depicted may be used in any capacity as a medical implant in various embodiments. For example, and without limitation, the medical implant 1 may be an interbody spinal spacer configured to provide support between two adjacent vertebra while the vertebra fuse together. A first side 11 is shown on top in FIG. 1, and a second side 12 is on bottom. The first side 11 and the second side 12 may be angled relative to one another to assist with controlling sagittal and coronal curvatures of a spine. Additionally, one or more larger openings (not shown) may be created between the first side 11 and the second side 12 for various purposes, including providing a path for additional bone growth and providing a chamber capable of retaining bone growth promoting substances and carriers. Openings may also be created transverse to the larger opening described immediately above, and may be present in combination with or in lieu of the larger opening. Some embodiments may include teeth or other surface features that assist with fixation between an implant and an adjacent musculoskeletal structure. Examples include but are not limited to, teeth, spikes, ridges, projections of any type, indentations, roughening, knurling, or any other device for enhancing fixation, penetrating, or capturing a portion of tissue relative to an implant.

Similar devices may be fabricated for spacing apart other musculoskeletal structures, for filling voids in bone, or for any other effective surgical purpose. Other shapes and sizes of a porous scaffold and bioactive material are within the scope of the invention. For example and without limitation, devices shaped to fill a spinal facet joint, a void left in an iliac crest following removal of autograft, a void associated with a dental surgical procedure, a void left from diseased bone or bone subjected to trauma, or one or more prosthetic vertebral bodies may be fabricated with some or all of the features of embodiments of the invention.

Embodiments of the invention include a porous scaffold 10 with one or more pores or tunnels. The one or more tunnels may pass more than half way through the medical implant 1. For example, the tunnels may pass in either or both directions more than half way between the first side 11 and the second side 12. Multiple pores of some embodiments of the porous scaffold define open volumes that connect at least between the first side 11 and the second side 12. The scaffold structure volume, or solid portion of the porous scaffold 10 of some embodiments, is between about 30% and 80% of a volume occupied by the porous scaffold 10. The term the volume occupied by the porous scaffold 10 means the volume defined by edges that generally pass through the outer extents of the porous scaffold 10. The multiple pores noted above of some embodiments include walls that define the interfaces between the scaffold structure and the multiple pores though the scaffold structure.

Embodiments of the porous scaffold 10 in whole or in part may be constructed of biocompatible materials of various types. Examples of porous scaffold materials include, but are not limited to, non-reinforced polymers, carbon-reinforced polymer composites, metals, ceramics and combinations thereof. In some embodiments, the scaffold structure or individual components of the scaffold structure may be constructed of sections of bone or other tissues. Tissue materials include, but are not limited to, autograft, allograft, or xenograft, and may be resorbable or non-resorbable in nature. Examples of other tissue materials include hard tissues, connective tissues, demineralized bone matrix, and combinations thereof.

Biocompatible polymers may be obtained from natural or synthetic sources, and may be bioresorbable. Collagen, elastin, silk, and demineralized bone matrix are non-limiting examples of materials that may in whole or in part comprise natural biocompatible polymers. Examples of non-resorbable synthetic materials include polyethylene, low density polyethylene, polymethylmethacrylate (PMMA), polyetheretherketone (PEEK), polyetherketoneketone (PEKK), polyurethane homopolymers, co-polymers and oligomers of polyhydroxy acids, polyesters, polyorthoesters, polyanhydrides, polydioxanone, polydioxanediones, polyesteramides, polyaminoacids, polyamides, polycarbonates, polylactide, polyglycolide, tyrosine-derived polycarbonate, polyanhydride, polyorthoester, polyphosphazene, polyethylene, polyester, polyvinyl alcohol, polyacrylonitrile, polyamide, polytetrafluorethylene, poly-paraphenylene terephthalamide, polyaryletherketones, polyetherketones, cellulose, carbon fiber reinforced composite, and mixtures thereof. The polymer may also be a polymeric hydroxyethylmethacrylate (PHEMA). The polymeric hydroxyethylmethacrylate may include a copolymer of monomeric hydroxyethylmethacrylate and a cross-linking agent. The cross-linking agents may include triethyleneglycol dimethacrylate, tetraethyleneglycol dimethacrylate, diethyleneglycol dimethacrylate, and monoethyleneglycol dimethacrylate. The cross-linking agents may comprise from about 0.1% to about 5% by weight of the monomeric hydroxyethylmethacrylate. "Biocompatible" as used herein means that a material will not cause substantial tissue irritation or necrosis at the target tissue site.

Suitable bioresorbable synthetic polymers include poly(L-lactide), poly(D,L-lactide), poly(L-co-D,L-lactide), polyglycolide, poly(lactide-co-glycolide), poly(hydroxylbutyrate), poly(hydroxyvalerate), tyrosine-derived polycarbonate, polyanhydride, polyorthoester, polyphosphazene, poly(dioxanone), and polyglyconate. Other similar polymers known to the art may be used and various mixtures of polymers may be combined to adjust the properties of the composition as desired. "Bioresorbable" materials specified herein include both bioerodible and bioabsorbable materials; where "bioerodible" refers to a material that will erode or degrade over time due, at least in part, to contact with substances found in the surrounding tissue, fluids or by cellular action; and "bioabsorbable" refers to a material that will be broken down and absorbed within the human body, for example, by a cell or tissue.

Metals that can be used to form the scaffold structure of the porous scaffold 10 include but are not limited to stainless steel and other steel alloys, cobalt chrome alloys, tantalum, titanium, titanium alloys, titanium-nickel alloys such as Nitinol and other superelastic or shape-memory metal alloys. Metals can be formed into supportive frameworks by a variety of manufacturing procedures including combustion synthesis, plating onto a "foam" substrate, chemical vapor deposition (see U.S. Pat. No. 5,282,861), lost mold techniques (see U.S. Pat. No. 3,616,841), foaming molten metal (see U.S. Pat. Nos. 5,281,251, 3,816,952 and 3,790,365), and replication of reticulated polymeric foams with a slurry of metal powder.

Sintering of metals and polymers of various types and other methods of forming porous structures may be accomplished as disclosed at least in U.S. Pat. Nos. 6,572,619, and 6,673,075, which are hereby incorporated by reference. Combinations of the materials noted above for use in making the porous scaffold may be used in any effective amount or assembly.

Embodiments of the medical implant 1 include a bioactive material 20 applied to the porous scaffold 10. In some embodiments, the bioactive material is, on average, less than about ten microns thick on substantially all of the walls of the multiple pores of the porous scaffold. By specifying application of the bioactive material 20 on substantially all of the walls, it is meant herein that at least some bioactive material 20 is applied somewhere along substantially each path through the medical implant 1, and not that all lengths along substantially every wall through every juncture must receive bioactive material 20. It should be recognized that in various embodiments, the multiple pores have irregular shapes that may depart and rejoin with other pores and that may or may not define a path all of the way through the medical implant 1.

In some embodiments, the bioactive material 20 is deposited in a thickness of less than about ten microns on the interior wall of one or more of the tunnels or pores at least half way through the medical implant 1. The application of the bioactive material 20 may occur through the first side 11, through the second side 12, or through both the first and second sides 11, 12 in various embodiments. The bioactive material 20 may be applied completely through the medical implant 1 from one side or may be applied part of the way through from one side and part of the way through from the other side. Some embodiments of the medical implant 1 include multiple paths through the pores between the first side 11 and the second side 12 that remain at least in part open for unobstructed passage of fluid through the porous scaffold 10 and the bioactive material 20. An open passage may more readily allow for transmission of fluids that carry materials effective in the remodeling and building of bony tissue. A passage completely through the medical implant 1 may serve to facilitate bone growth entirely through the medical implant 1 and not merely into a portion of the medical implant 1 that is adjacent to bone.

Some embodiments include depositing a bioactive material 20 by spraying the bioactive material 20 on an interior wall of one or more of the tunnels at least half way through the medical implant 1 between the first side 11 and the second side 12. The bioactive material 20 may be sprayed to a thickness of less than about 100 microns. This spraying thickness may be particularly compatible with some methods of plasma spraying the bioactive material 20. For other embodiments, the bioactive material 20 may be sprayed to a thickness of less than about 10 microns.

The bioactive material 20 may be an osteoconductive material. Examples of osteoconductive materials include various bioceramic materials, calcium phosphate and other members of the calcium phosphate family, fluorapatite, bioactive glass, and collagen-based materials. Members of the calcium phosphate family include materials such as hydroxyapatite, α-tricalcium phosphate, β-tricalcium phosphate, tetracalcium phosphate, dicalcium phosphate dihydrate, ocatacalcium phosphate, and the like.

The bioactive material 20 may include an osteoinductive or osteogenic material. Examples of such substances include demineralized bone matrix, osteoblast cells, platelet-derived growth factors (PDGFs), bone morphogenetic proteins (BMPs), insulin-like growth factors (IGFs), basic fibroblast growth factor (bFGF), cartilage derived morphogenetic protein (CDMP), growth and differentiation factors (GDFs), LIM mineralization proteins, transforming growth factor beta family (TGF-β), and other bone proteins, such as CD-RAP. These proteins can be recombinantly produced or obtained and purified from an animal that makes the proteins without the use of recombinant DNA technology. Recombinant human BMP is referred to as "rhBMP"; recombinant human GDF is referred to as "rhGDF". Mimetics of these growth factors can also be used in the devices of the present invention for inducing the growth of bone.

Examples of BMPs and GDFs known to have osteogenic, chondrogenic and other growth and differentiation activities and are suitable for this invention include, but are not limited to, BMP-2, rhBMP-2, BMP-3, rhBMP-3, BMP-4 (also referred to as BMP-2B), rhBMP4 (also referred to as rhBMP-2B), BMP-5, rhBMP-5, BMP-6, rhBMP-6, BMP-7 (OP-1), rhBMP-7 (rhOP-1), BMP-8, rhBMP-8, BMP-9, rhBMP-9, BMP-12, rhBMP-12, BMP-13, rhBMP-13, BMP-15, rhBMP-15, BMP-16, rhBMP-16, BMP-17, rhBMP-17, BMP-18, rhBMP-18, GDF-1, rhGDF-1, GDF-3, rhGDF-3, GDF-5, rhGDF-5, GDF-6, rhGDF-6, GDF-7, rhGDF-7, GDF-8, rhGDF-8, GDF-9, rhGDF-9, GDF-10, rhGDF-10, GDF-11, rhGDF-11, GDF-12, rhGDF-12, GDF-14 and rhGDF-14. BMP-2, BMP-3, BMP-4, BMP-5, BMP-6 and BMP-7 are disclosed in U.S. Pat. Nos. 5,108,922; 5,013,649; 5,116,738; 5,106,748; 5,187,076; and 5,141,905; BMP-8 is disclosed in PCT publication WO91/18098; BMP-9 is disclosed in PCT publication WO93/00432; BMP-10 is disclosed in U.S. Pat. No. 5,637,480; BMP-11 is disclosed in U.S. Pat. No. 5,639,638; BMP-12 and BMP-13 are disclosed in U.S. Pat. No. 5,658,882; BMP-15 is disclosed U.S. Pat. No. 5,635,372; and BMP-16 is disclosed in U.S. Pat. Nos. 5,965,403 and 6,331,612. Growth and differentiation factors (GDFs) are described in PCT applications WO94/15965; WO94/15949; WO95/01801; WO95/01802; WO94/21681; WO94/15966; WO95/10539; WO96/01845; WO96/02559 and others. All of the afore-mentioned references are incorporated herein by reference.

Each BMP may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in PCT application WO 93/09229. The amount of osteogenic protein useful herein is an amount which is effective to stimulate increased osteogenic activity of infiltrating progenitor cells and will depend upon several factors including the size and nature of the defect being treated, the bone regeneration device, and the particular protein being employed.

The bioactive material 20 may also include BIP which is disclosed in WO94/01557, HP00269 which is disclosed in JP Publication number: 7-250688 and/or MP52 which is disclosed in PCT application WO93/16099. Other agents that can be included in the devices of the present invention include heterodimers of the above-mentioned growth factors, modified proteins, partial deletion products and mimetic agents. These proteins may be used individually or in mixtures of two or more.

One or more statins may also be included in the bioactive material 20. Statins are 3-hydroxy-3-methylglutaryl coenzyme A reductase (a.k.a. HMG-CoA reductase) inhibitors and have been shown to induce bone formation in certain subjects. Non-limiting examples of statins that may be included in the devices of the present invention include atorvastatin, cerivastatin, fluvastatin, lovastatin, mavastatin, pitavastatin, pravastatin, rosuvastatin and simvastatin.

The bioactive material 20 may include various other organic species known to induce bone formation, and combinations thereof, or other therapeutic agents. The bioactive material 20 may also or in addition include pharmaceuticals that target infection or particular cells, such as but not limited to, bacterial or viral infections or cancer cells.

In some embodiments, the bioactive material 20 is, by volume, between 0.5% and 30% of the medical implant 1. The bioactive material 20 may include one of more of osteoconductive, osteogenic, osteoinductive, and carrier or adhesive components as a portion of its volume. The components may be applied, solely, simultaneously, or sequentially. The bioactive material 20 may include a combination of a first layer of osteoconductive material and a second layer of osteoinductive or osteogenic material. The layers may be applied in separate processes or the layers may include combinations of materials at least partially mixed prior to application to the porous scaffold 10. The layer may be applied by spraying, dipping the porous scaffold in a solution, or by any effective process.

An embodiment of the medical implant 1 includes a first side 11 and an opposite second side 12. The medical implant 1 may include a support means with one or more tunnels that pass more than half way through the medical implant 1 between the first side 11 and the second side 12. The medical implant 1 may also include a bioactive means deposited on an interior wall of one or more of the tunnels at least half way through the medical implant 1 between the first side 11 and the second side 12. The bioactive means may be any bioactive material 20 disclosed herein applied in any effective way on the interior walls.

The act of depositing bioactive material 20 on or in the porous scaffold 10 may be accomplished in any effective way. In general, the act of depositing bioactive material 20 requires depositing or spraying one or more very thin applications of material. As noted above, in some embodiments the bioactive material 20 is applied on one or more walls of the pores or tunnels at least half way through a medical implant 1 between the first side 11 and the second side 12 at a controlled thickness. Consequently, the bioactive material 20 must be applied in a forceful but controlled manner. For some embodiments, the act of depositing the bioactive material 20 results in at least one tube of bioactive material 20 with an average wall thickness of no more than about 10 microns that connects between the first side 11 and the second side 12. A number of methods of depositing material may be used in association with various embodiments of the invention, some of which are specified in more detail below.

Example techniques for depositing or spraying bioactive material 20 that may be used with various embodiments include Ion Beam Deposition (IBD) or Ion Beam Assisted Deposition (IBAD), Ion Beam Induced Deposition, Cold Spray techniques, High Velocity Oxy-Fuel (HVOF) techniques, Vacuum Plasma Spraying (VPS), Arc Spray techniques, Cathodic Arc Deposition, Sputter Deposition, Plasma Spray, and Atmospheric Plasma Spray. The IBD or IBAD techniques include applying materials to a target by using an ion beam. Ion implantation may be combined with either simultaneous sputtering or similar physical vapor deposition processes. The IBAD process provides for independent control of critical process parameters such as ion energy, temperature, and pressure. Therefore it is easier to avoid damaging the substrate and the bioactive material. Utilization of this process may produce a gradual transition between the substrate material and bioactive material with less strain and a more durable bond between the bioactive material 20 and the porous scaffold 10. With ion source techniques, gases or evaporated solids are ionized using electron ionization or by application of high electric fields. An example ion source device is a Penning ion generator.

A method useful in some embodiments is the Cold Spray process where the materials are at or near room temperature until impact. With a Cold Spray method, the bioactive material 20 is bombarded against the porous scaffold 10 at speeds between 500-1500 meters per second. A metallurgical bond or bond induced by kinetic energy of the propelled bioactive material 20 is formed without imposing a chemical change in the substrate or inducing some stresses associated with thermal processes.

A Cathodic Arc Deposition system may be used to apply bioactive material 20 to the porous scaffold 10 in some embodiments. With a Cathodic Arc Deposition system, a high voltage arc is created that blasts ions out of a solid source material. The ions are then accelerated and focused using high voltage. Optional deceleration at the substrate can be employed to select particular deposition energies.

As noted above, the Plasma Spray process may be useful to deposit relatively thicker coatings of bioactive material 20. With a Plasma Spray method, a high frequency arc is ignited between an anode (nozzle) and a cathode (electrode). Process gases, generally mixtures of argon, nitrogen, hydrogen and helium, flowing between the anode and cathode are ionized to become a plume of hot plasma gas with that may reach 6,600° C. to 16,600° C. (12,000° F. to 30,000° F.). When a coating material such as bioactive material 20 is injected into the gas plume, it is melted and propelled towards the target substrate.

Example

Example medical implants 1 were made and evaluated as follows. An example method of manufacturing includes providing a porous scaffold 10. The porous scaffold may be formed from PEEK particles sized between 100 microns and 600 microns. The example porous scaffold 10 was made with 300-600 micron PEEK particles that were ground from standard PEEK pellets using a polymer grinder and sifted with sieves to achieve the desired particle size. The PEEK particles were weighed prior to placing the PEEK particles in a compression mold. The amount of PEEK particles place in the compression mold was 0.3-0.4 grams. The mold had an approximately 13 mm inside diameter and was 10 mm tall. The mold included a circular base and a top with a 12.9 mm diameter and a 5 mm protrusion for compressing the PEEK particles within the mold in response to pressure applied to the top and bottom of the mold.

A Carver Press was used to compress the PEEK particles in the compression mold. The Carver Press included a base platen and a top platen. Both platens were preheated to about 316-371° C. (600-700° F.). The top platen was lowered until an approximately 45 kg (100 lb) compressive load was applied to the compression mold. The PEEK particles were allowed to remain under compressive load for 10-15 minutes. The compressive load was removed, and the mold was allowed to cool for an additional 10 minutes prior to removing the sintered porous scaffold from the mold. Various porosity implants were produced, ranging from 42-71% PEEK by volume. The medical implant 1 illustrated in FIG. 1 is approximately 71% PEEK by volume and is 29% porous, excluding the application of the bioactive material 20.

An alternative method of producing porous scaffolds includes the use of an oven. In this alternative method, 300-600 micron PEEK particles are placed into a mold. A weight or compressive clamp is placed on the mold to achieve appropriate compression of the PEEK particles. The mold is then placed in a cold oven and the oven is progressively ramped to a temperature of approximately 343° C. (650° F.) over a period of six hours. The mold is removed and allowed to cool prior to removing the sintered porous scaffold produced by the process.

Returning to the specific example, a bioactive material 20 was deposited on the porous scaffold using an IBAD process. The bioactive material 20 of the example devices was hydroxyapatite. Hydroxyapatite was deposited throughout the porous scaffold 10, as shown in FIG. 2. The hydroxyapatite applied included both nano and microcap hydroxyapatite. Various percentages of hydroxyapatite were applied in testing, ranging from 1-15% by volume. As illustrated in FIGS. 1 and 2, the hydroxyapatite bioactive material 20 made up approximately 14.5% of the medical implant 1.

The example medical implant 1 was evaluated in light of its response to the growth of cell cultures applied to the medical implant 1. In particular, a cell culture of human stem cells (hMSC) was applied to the medical implant 1. An increase in hydroxyapatite in the medical implant 1 in response to the application of hMSCs would show responses by hMSCs that indicate the hMSCs are in an environment that supports or promotes bone growth activity. More specifically, hMSCs that are stimulated by the environment in which they are placed to engage in bone forming activities will produce measurably higher levels of hydroxyapatite. Therefore, higher measurements of hydroxyapatite in samples to which hMSCs were applied would show increased bone growth activity and increased support for the formation of bone if the hMSCs were received in an environment that was favorable to bone growth. Thus, the amount of hydroxyapatite in samples to which hMSCs was applied compared to the amount of hydroxyapatite of samples made by the same process is an indicator of whether a sample made by the process is conducive to bone growth activity.

To evaluate responses of particular medical implant samples to hMSCs, consistent amounts of hMSCs were placed on the top of medical implants and allowed to migrate under the force of gravity through the hydroxyapatite coated porous scaffolds. Cell responses were given time to occur. The medical implants were subsequently evaluated for the presence of hydroxyapatite. A comparison was made for the presence of hydroxyapatite between at least one implant made by a particular process, but that did not have hMSCs applied, to at least one implant made by the same process that did have hMSCs applied. The result of the comparisons was that the medical implants to which hMSCs were applied included an average of about 67% more hydroxyapatite than medical implants made from the same processes to which no hMSCs had been applied. Specifically, the average number of cubic millimeters of hydroxyapatite per implant for implants that had not received hMSCs was 90 mm$^3$. The average number of cubic millimeters of hydroxyapatite per implant for implants that had received hMSCs was 150 mm$^3$. Therefore, the example implants were found to provide an environment that was favorable to bone growth.

Various method embodiments of the invention are described herein with reference to particular medical implants. However, in some circumstances, each disclosed method embodiment may be applicable to each of the medical implants, or to some other implant operable as disclosed with regard to the various method embodiments.

Terms such as top, bottom, side, down, height, tall and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A medical implant having a first side and an opposite second side comprising:
   a porous scaffold comprised of polyether ether ketone having multiple pores defining open volumes that connect at least between the first side and the second side, wherein the porous scaffold includes a scaffold structure comprised of sections of bone or other tissues and wherein the multiple pores include walls defining interfaces between the scaffold structure and the pores, wherein the scaffold structure is bioresorbable; and
   a bioactive material on average less than about ten microns thick that is coupled to substantially all of the walls of the porous scaffold, wherein the bioactive material comprises a statin;
   wherein multiple paths through the pores between the first side and the second side remain at least in part open for passage of a fluid through the porous scaffold and the bioactive material, and
   wherein at least one of the first or opposite second sides of the medical implant include surface features for enhancing fixation, penetration, or capturing a portion of tissue selected from the group consisting of teeth, spikes, ridges, projections, indentations, roughening, knurling or combinations thereof, and the porous scaffold comprises by volume excluding the bioactive material of polyether ether ketone having an initial particle size of 300 to 600 microns.

2. The medical implant of claim 1 wherein the bioactive material is, by volume, between one percent and fifteen percent of the medical implant.

3. The medical implant of claim 1 wherein the bioactive material is an osteoinductive material.

4. The medical implant of claim 1 wherein the bioactive material is an osteoconductive material.

5. The medical implant of claim 1 wherein the bioactive material includes bone morphogenetic protein.

6. The medical implant of claim 1 wherein the bioactive material includes a biomaterial from the calcium phosphate family.

7. The medical implant of claim 1 wherein the bioactive material includes a first layer of osteoconductive material and a second layer of osteoinductive material.

8. A medical implant having a first side and an opposite second side comprising:
   a porous scaffold comprised of polyether ether ketone having multiple pores defining open volumes that connect at least between the first side and the second side, wherein the porous scaffold includes a scaffold structure comprised of metal, and wherein the multiple pores include walls defining interfaces between the scaffold structure and the pores wherein the scaffold structure is not bioresorbable; and
   a bioactive material on average less than about ten microns thick that is coupled to substantially all of the walls of the porous scaffold, wherein the bioactive material comprises a statin;
   wherein multiple paths through the pores between the first side and the second side remain at least in part open for passage of a fluid through the porous scaffold and the bioactive material, and
   wherein at least one of the first or opposite second sides of the medical implant include surface features for enhancing fixation, penetration, or capturing a portion of tissue selected from the group consisting of teeth, spikes, ridges, projections, indentations, roughening, knurling or combinations thereof, and the porous scaffold comprises by volume excluding the bioactive material of polyether ether ketone having an initial particle size of 300 to 600 microns.

9. The medical implant of claim 8, wherein the metal is selected from the group consisting of: stainless steel, steel alloys, cobalt chrome alloys, tantalum, titanium, titanium alloys, titanium nickel alloys, superelastic metal alloys, shape-memory metal alloys, and combinations thereof.

10. The medical implant of claim 8, wherein the bioactive material is, by volume, between one percent and fifteen percent of the medical implant.

11. The medical implant of claim 8, wherein the bioactive material is an osteoinductive material.

12. The medical implant of claim 8, wherein the bioactive material is an osteoconductive material.

13. The medical implant of claim 8, wherein the bioactive material includes bone morphogenetic protein.

14. The medical implant of claim 8, wherein the bioactive material includes a biomaterial from the calcium phosphate family.

15. The medical implant of claim 8, wherein the bioactive material includes a first layer of osteoconductive material and a second layer of osteoinductive material.

16. The medical implant of claim 8, wherein the bioactive material includes hydroxyapatite.

17. The medical implant of claim 16, wherein the hydroxyapatite includes nano and micro calcium phosphate hydroxyapatite.

18. The medical implant of claim 8, wherein the first side and the second side are angled relative to one another.

* * * * *